United States Patent
Court et al.

(10) Patent No.: US 8,217,218 B2
(45) Date of Patent: Jul. 10, 2012

(54) PROBE FOR FLUID LEAK DETECTION WITH SPECIFIC DISTAL PART

(75) Inventors: Thierry Court, Villeurbanne (FR); Jean Michel Goby, Sennecey les Dijon (FR); Jean Pierre Anselmet, Dijon (FR)

(73) Assignee: Gambro Lundia AB (SE)

( * ) Notice: Subject to any disclaimer, the term of this patent is extended or adjusted under 35 U.S.C. 154(b) by 19 days.

(21) Appl. No.: 12/922,400

(22) PCT Filed: Mar. 4, 2009

(86) PCT No.: PCT/IB2009/000419
§ 371 (c)(1),
(2), (4) Date: Dec. 3, 2010

(87) PCT Pub. No.: WO2009/112912
PCT Pub. Date: Sep. 17, 2009

(65) Prior Publication Data
US 2011/0071367 A1    Mar. 24, 2011

(30) Foreign Application Priority Data
Mar. 14, 2008  (FR) ...................................... 08 01387

(51) Int. Cl.
*A61F 13/15* (2006.01)
*A61B 5/00* (2006.01)

(52) U.S. Cl. ........ 604/361; 600/300; 600/382; 600/393; 600/395; 340/605; 340/620

(58) Field of Classification Search ............... 604/65, 604/304, 307–308, 361; 600/300, 372–373, 600/382, 384, 386, 393, 396, 506, 547; 340/605, 340/618, 620
See application file for complete search history.

(56) References Cited

U.S. PATENT DOCUMENTS

| | | | | |
|---|---|---|---|---|
| 5,557,263 | A | * | 9/1996 | Fisher et al. .................. 340/605 |
| 5,579,765 | A | * | 12/1996 | Cox et al. ....................... 600/307 |
| 5,964,703 | A | * | 10/1999 | Goodman et al. ............ 600/382 |
| 6,175,310 | B1 | * | 1/2001 | Gott .............................. 340/605 |
| 2002/0190840 | A1 | | 12/2002 | Fujita et al. |
| 2005/0177062 | A1 | | 8/2005 | Skrabal et al. |
| 2007/0139155 | A1 | | 6/2007 | Chung et al. |
| 2007/0182791 | A1 | | 8/2007 | Chung et al. |

FOREIGN PATENT DOCUMENTS

| | | |
|---|---|---|
| FR | 2 737 124 | 1/1997 |
| JP | 55-31983 | 3/1980 |
| WO | WO 99/26686 | 6/1999 |

* cited by examiner

*Primary Examiner* — Quynh-Nhu H Vu
(74) *Attorney, Agent, or Firm* — Finnegan, Henderson, Farabow, Garrett & Dunner LLP

(57) ABSTRACT

A disposable medical probe for detecting a leak of physiological fluid comprising a support layer, a conductive layer on top of the support layer, the conductive layer comprising two conducting electrodes both placed exclusively on each side of a longitudinal axis, the conductive layer defining two zones: a proximal zone with two proximal electrode parts being placed parallel to each other and being spaced apart by a constant distance d, and a distal zone with two distal electrode parts being spaced apart from each other by a gap e greater than said distance d, where the distal zone of the electrodes defines an increase in the gap between the distal parts of the electrodes, followed by a decrease in the gap between the distal parts of the electrodes.

28 Claims, 9 Drawing Sheets

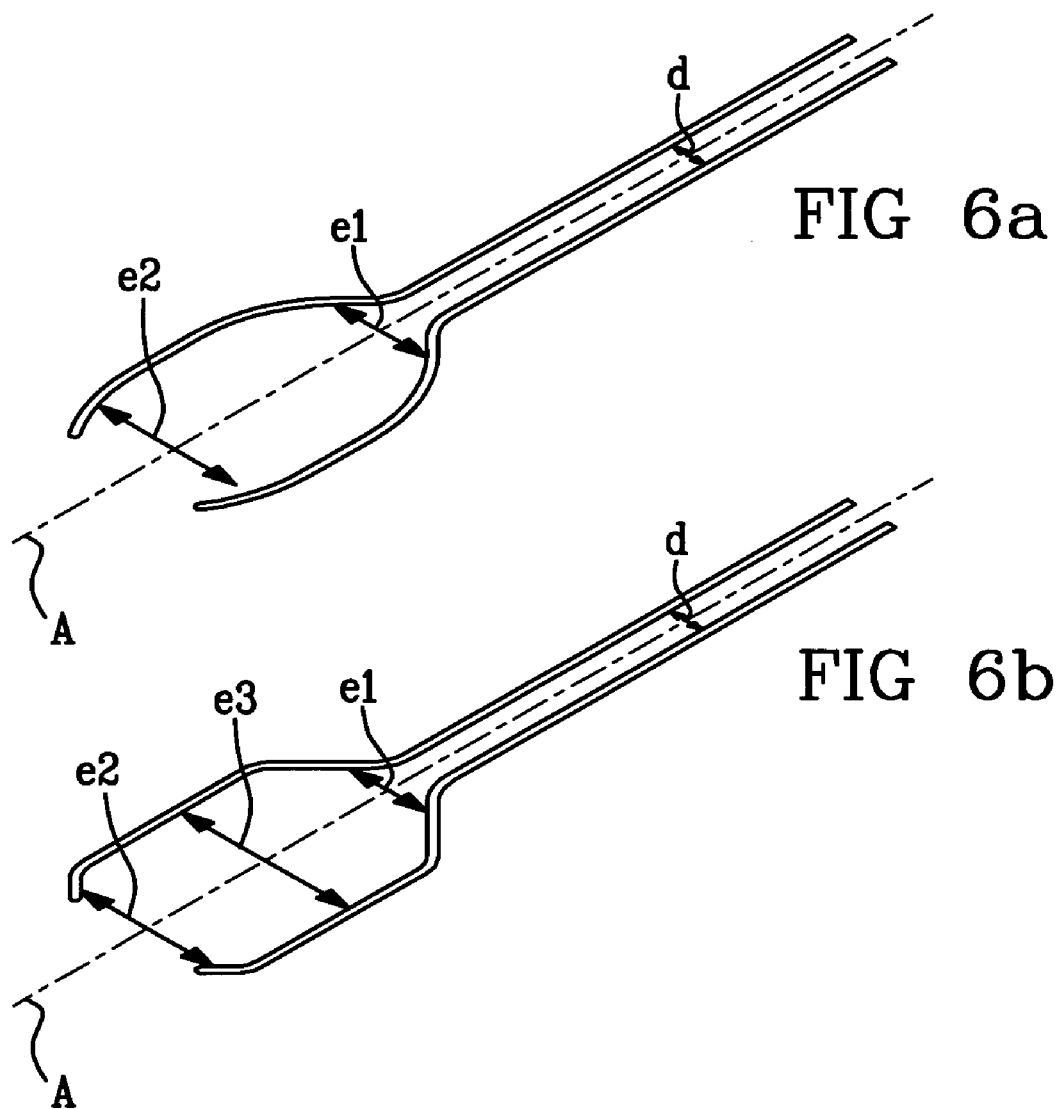

PROBE FOR FLUID LEAK DETECTION WITH SPECIFIC DISTAL PART

CROSS REFERENCE TO RELATED APPLICATIONS

This application is a national phase application based on PCT/IB2009/000419 filed Mar. 4, 2009, which claims the benefit of French Patent Application No. FR 08/01387, filed Mar. 14, 2008, the contents of all of which are incorporated herein by reference.

TECHNICAL FIELD OF THE INVENTION

The present invention relates to a probe for detecting a leak or the presence of an electrically conductive fluid, such as blood or plasma, and to its method of manufacture.

The invention has an application particularly in the field of extracorporeal treatment of blood or plasma, where blood is withdrawn from and returned to the patient for the entire duration of a session.

PRIOR ART

In all treatments requiring perfusion of a fluid, and similarly in treatments of blood (hemodialysis, hemofiltration, for example) and in methods for removing a component of the blood (apheresis, plasmapheresis, for example) where the blood of a patient or of a donor is circulated outside the body, a fluid is injected into a cavity or body conduit of the patient or donor by means of a channel having one end connected to a source of fluid and another end connected to a tube, such as a cannula or a catheter, with a shape, a length, a flexibility or a rigidity that are chosen to facilitate penetration of the tube into a conduit or a given cavity.

In the case of the aforementioned treatments of blood and methods of removing a blood component, the source of fluid is formed by the vascular circuit of the patient/donor, and the fluid is the blood of the patient/donor, which blood, pumped in an artery, is caused to circulate in a blood treatment apparatus (hemodialyzer, hemofilter, plasma filter, centrifuge, etc.) and, once freed of its impurities or having a fraction of one of its components reduced, is re-injected into a vein of the patient/donor.

The tube, which is inserted into the conduit or body cavity, is generally held in place by means of a piece of adhesive tape placed over the channel in order to bind it to the patient's body.

It can happen that the adhesive tape comes unstuck and, as a result of the movements of the patient/donor, the tube comes completely or partially out of the cavity or conduit into which it had been inserted. It can also happen that the patient/donor, who is drowsy for example, does not notice the removal of the tube from the cavity or conduit. The incident may prove fatal, especially when the fluid injected into the patient/donor is his own blood.

A first invention concerning detection of physiological fluid is described in the patent FR 2 737 124, which is incorporated here by way of reference and of which the device is shown in FIGS. 1 and 2. It is a device for detecting accidental removal of a tube (2, 3, 29) that has been inserted into a conduit or a body cavity of a patient, the tube being connected via a channel to a source (1, 21) of a fluid circulating in the direction of the tube. Said device comprises means for detecting an effusion of fluid near the site of penetration of the tube into the patient's body. The means for detecting an effusion of fluid comprise a probe 7 which is sensitive to a physical or chemical characteristic of the fluid, is able to emit a corresponding signal and is intended to be affixed to the patient's body near the site of penetration of the tubular body into the patient's body, and means for processing the signal (9, 10) delivered by the probe. When the fluid contains an ionized substance (blood, saline solution), the probe is, for example, a probe for measuring conductivity or impedance. The probe comprises two electrodes that are connected to a control housing via two conducting wires 10, the control housing being connected to acoustic or luminous alarm means (12, 15), even to occlusion means 13 for closing the channel. The control housing comprises means for triggering an alarm and for causing occlusion of the channel when the voltage measured between the electrodes of the probe exceeds the predetermined threshold value and/or when the kinetics of evolution of this voltage exceed a predetermined threshold value. The inserted tube can be the end of the venous line of an extracorporeal blood treatment circuit, as is shown in FIG. 2.

The prior art also includes the probe described in patent U.S. Pat. No. 6,175,310, shown in FIGS. 3a and 3b, which discloses an apparatus for detecting the presence of electrically conductive fluids, of which the concept is similar to that described above, requiring the use of a probe (or sensor) in the form of a flat strip composed of a pair of electrodes (24, 26) which are of identical width, are extremely flat, parallel to each other and placed on a support layer 22. A particular embodiment of the leak detection strip, shown here in FIG. 3a, has streamlined conductors placed on the strip in order to facilitate connection to the device for measuring leaks, having different spacings between the terminals. Although this strip is very simple to manufacture, it has been found that its use is not optimal in terms of detecting a leak of fluid and maintaining the probe on the patient's arm.

Furthermore, the prior art includes U.S. Pat. No. 5,557,263 which discloses an apparatus for detecting the presence of electrically conductive fluids, the concept of which device is similar to that described above, and requiring the use of a probe (or sensor) composed of a pair of electrodes which are of identical width, are parallel to each other and are placed on an absorbent material, which has the shape of an elongate strip and which can be wound up on itself. The user is able to unroll the strip and cut it to the desired length.

The inventors have developed a probe that provides optimized detection and optimal user comfort for the patient.

DISCLOSURE OF THE INVENTION

To achieve the objective, the invention provides a disposable medical probe 1 for detecting a leak of physiological fluid through an opening made in the human body, by operating in conjunction with an electrical detection circuit, comprising the following layers:
  a support layer 10,
  a conductive layer 20 on top of the support layer 10, the conductive layer comprising two conducting electrodes (21, 22) both placed exclusively on each side of a longitudinal axis (A), the conductive layer defining two zones:
    a proximal zone 20', the end of which is intended to be connected to said circuit, composed of a proximal part (21', 22') of each electrode, the two proximal electrode parts being placed parallel to each other and being spaced apart by a constant distance d,
    a distal zone 20" intended for possible contact with the fluid, composed of a distal part (21", 22") of each electrode (21, 22), the two distal electrode parts being spaced apart from each other by a gap e greater than said distance d, where the distal zone 20" of the electrodes defines, running from the border 20A between the proximal zone and the distal zone to the end of the distal zone 20B:

an increase in the gap e1 between the distal parts of the electrodes, followed by a decrease in the gap e2 between the distal parts of the electrodes.

The distal zone represents the zone that will be farthest away from the electrical connector clip for forming the electrical detection circuit, while the proximal zone represents the zone that will be nearest to the electrical connector clip.

The invention also relates to a method for the manufacture of a disposable medical probe for detecting a leak of physiological fluid through an opening made in the human body, by operating in conjunction with an electrical detection circuit, comprising the following steps:

a) obtaining a support layer 10,
b) placing a conductive layer 20 on top of the support layer 10, the conductive layer comprising two conducting electrodes (21, 22) both placed exclusively on each side of a longitudinal axis (A), the conductive layer 20 defining two zones:

a proximal zone 20', the end of which is intended to be connected to said circuit, composed of a proximal part (21', 22') of each electrode, the two proximal electrode parts being placed parallel to each other and being spaced apart by a constant distance d, a distal zone 20" intended for possible contact with the fluid, composed of a distal part (21", 22") of each electrode (21, 22), the two distal electrode parts being spaced apart from each other by a gap e greater than said distance d, where the distal zone 20" of the electrodes defines, running from the border 20A between the proximal zone and the distal zone to the end of the distal zone 20B:

an increase in the gap e1 between the distal parts of the electrodes, followed by a decrease in the gap e2 between the distal parts of the electrodes.

BRIEF DESCRIPTION OF THE DRAWINGS

Reference will be made to the attached drawings, in which:

FIGS. 6a and 6b show two alternatives concerning the shape of the two electrodes according to the invention.

DETAILED DESCRIPTION OF EMBODIMENTS OF THE INVENTION

Figure 1:
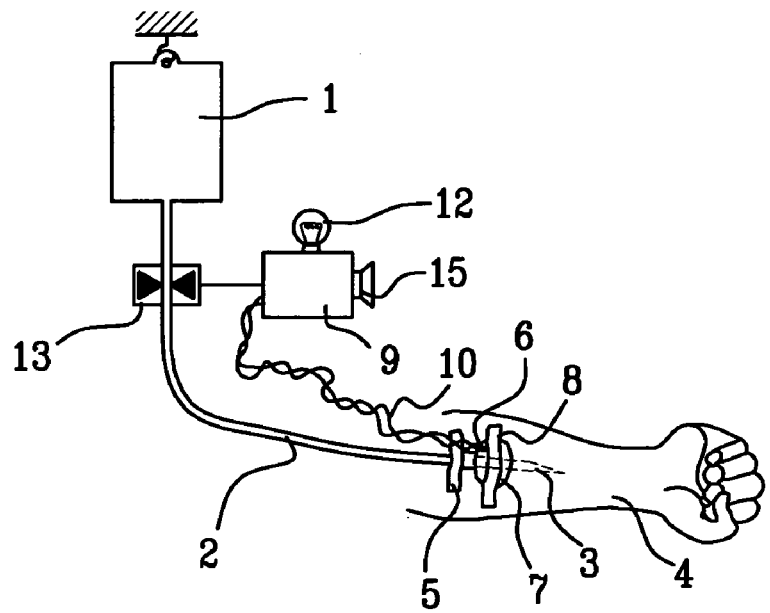
FIGS. 1 and 2 show the device described in prior art document FR 2 737 124.
Figure 2:
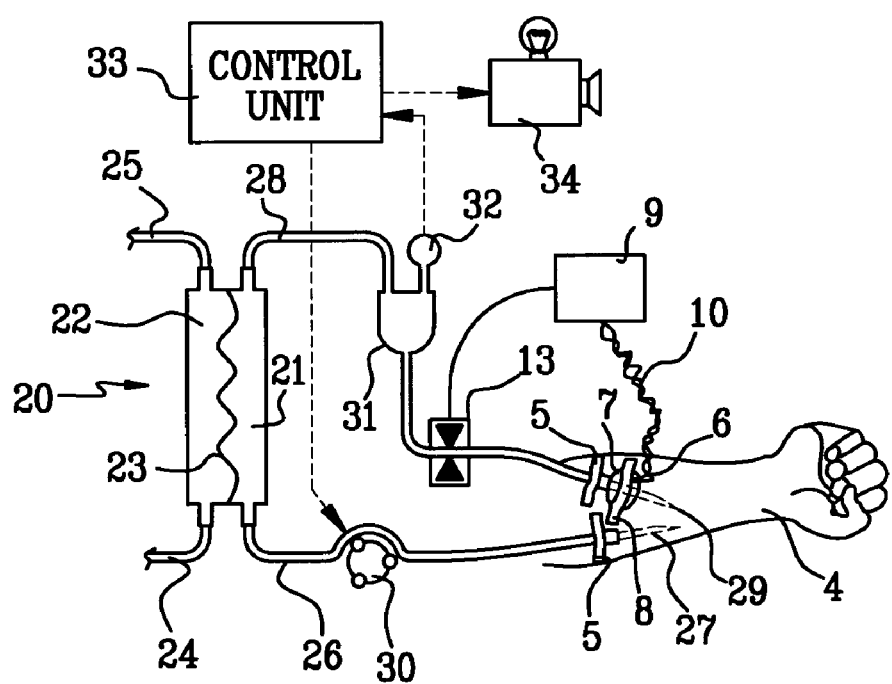
Figure 3A:
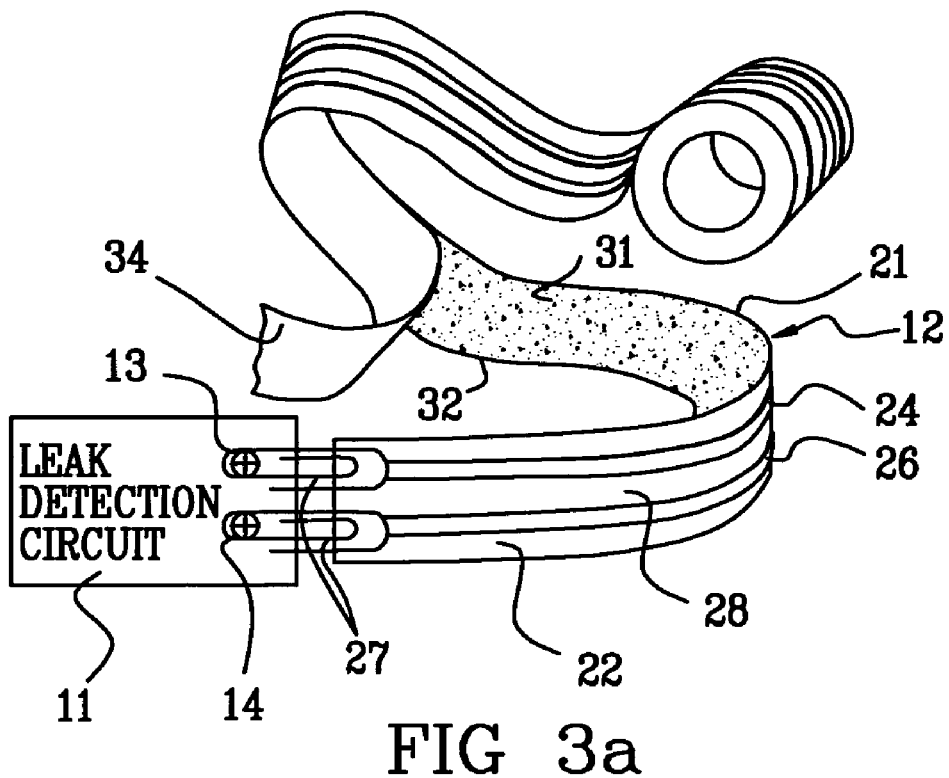
FIGS. 3a and 3b show the probe described in prior art document U.S. Pat. No. 6,175,310
Figure 3B:
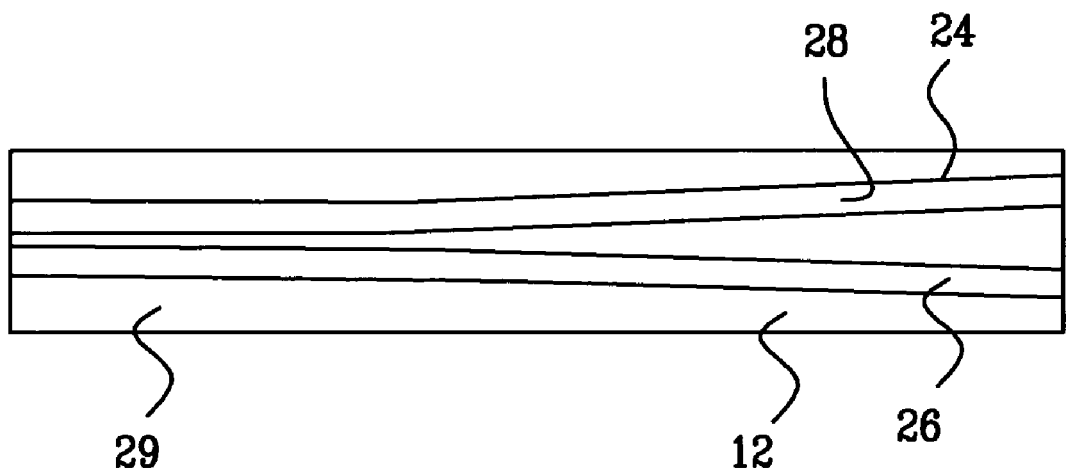
Figure 4:
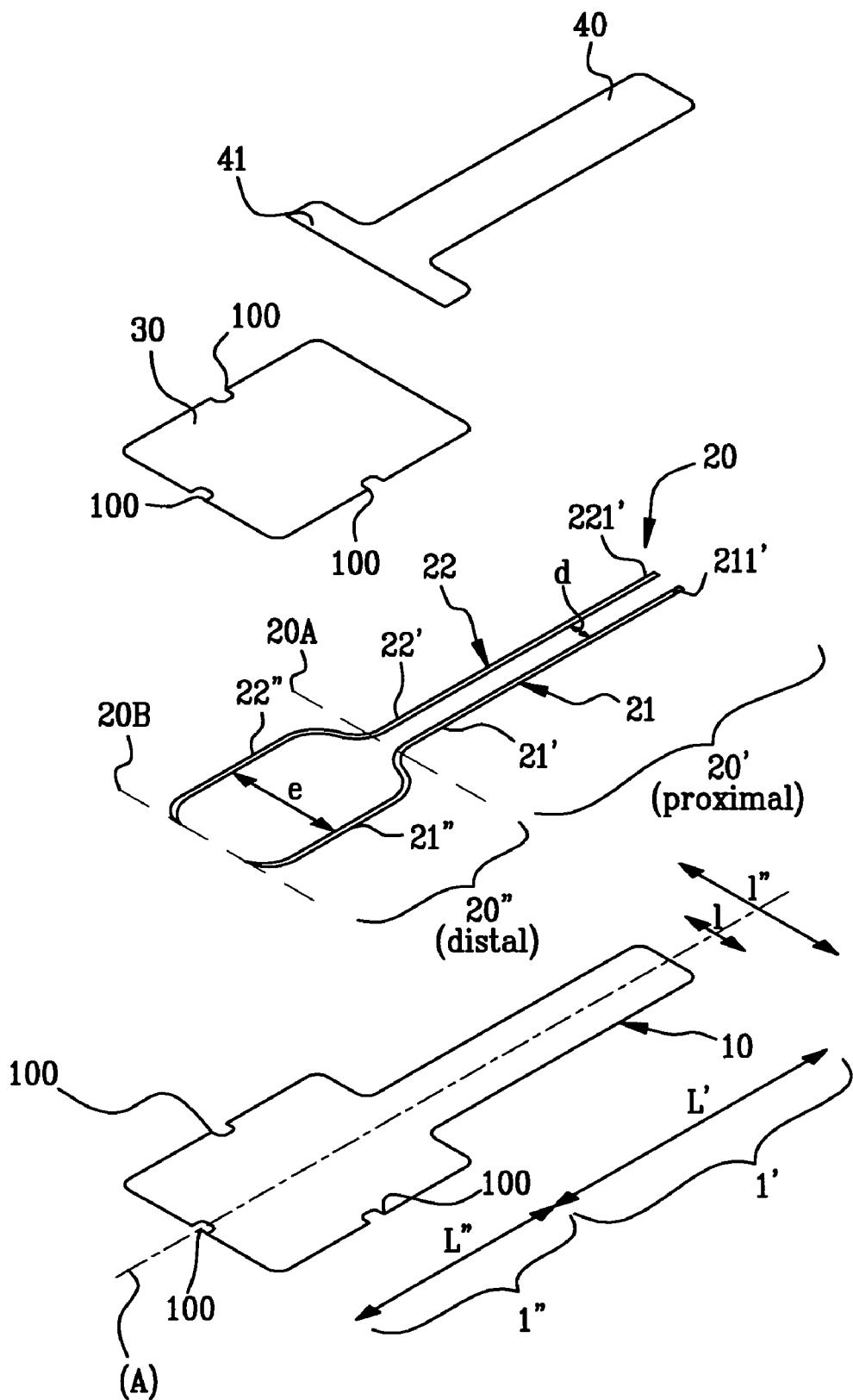
FIG. 4 shows an exploded view of one of the embodiments of the probe according to the invention that operates by detecting the resistance between the electrodes.

The disposable medical probe 1 for detecting a leak of physiological fluid through an opening made in the human body, by operating in conjunction with an electrical detection circuit, comprises the following layers:

a support layer 10,
a conductive layer 20 on top of the support layer 10, the conductive layer comprising two conducting electrodes (21, 22) both placed exclusively on each side of a longitudinal axis (A), the conductive layer defining two zones:

a proximal zone 20', the end of which is intended to be connected to said circuit, composed of a proximal part (21', 22') of each electrode, the two proximal electrode parts being placed parallel to each other and being spaced apart by a constant distance d, a distal zone 20" intended for possible contact with the fluid, composed of a distal part (21", 22") of each electrode (21, 22), the two distal electrode parts being spaced apart from each other by a gap e greater than said distance d, where the distal zone 20" of the electrodes defines, running from the border 20A between the proximal zone and the distal zone to the end of the distal zone 20B:

an increase in the gap e1 between the distal parts of the electrodes, followed by a decrease in the gap e2 between the distal parts of the electrodes.

The distal zone represents the zone that will be farthest away from the electrical connector clip for forming the electrical detection circuit, while the proximal zone represents the zone that will be nearest to the electrical connector clip.

It has in fact been found that a satisfactory gap between the two electrodes at the distal zone to be placed on the puncture site makes it possible to increase the "reception" area for leaking fluid in the distal zone and to optimize the detection of leaking of fluids without taking into account small quantities of conductive fluid (such as perspiration, for example, or a drop of blood due to the prior insertion of the needle) which lead to false alarms. Moreover, by having a distal electrode zone in which the gap increases (e1) and then decreases (e2), it is possible to provide a simple probe whose part with electrodes better surrounds the puncture site, irrespective of the location of the puncture site on the arm, irrespective of the position of the needle relative to the longitudinal axis of the probe, and irrespective of the angle of insertion of the needle.

Furthermore, the distance d will be smaller than any gap (e1, e2, e3) between the distal parts of the electrodes. By maintaining a shorter distance d in the proximal zone than the gap e in the distal zone, it is possible to provide a probe that is relatively flexible on the proximal part and that will fix itself and will remain fixed along the patient's arm, even with the movements made by the patient throughout the dialysis session, which lasts several hours.

The electrodes being "placed exclusively on each side of the longitudinal axis (A) of the conductive layer" means that the electrodes are each on one side of a longitudinal axis (A) contained in the plane of the electrodes and that the electrodes do not touch or cross this axis.

According to the invention, there can be a constant gap e3 between the distal parts of the electrodes, present between said increase in the gap e1 and said decrease in the gap e2. The distal electrode parts where the gap e3 is constant are parallel to the proximal parts of the electrodes.

The probe according to the invention can have the longitudinal axis (A) which is an axis of symmetry of substantially the entirety of the two electrodes (21, 22), hence overall of the whole conductive layer 30. The distal part of the electrodes is in this case entirely symmetrical with respect to the longitudinal axis (A).

According to the preceding feature, the probe can be a longitudinal probe extending along the longitudinal axis (A) of the probe. This permits a secure hold along the patient's arm.

This axis of symmetry of the two electrodes can represent the axis of symmetry of substantially the entire probe. The distal part of the probe is in this case entirely symmetrical with respect to the longitudinal axis (A).

According to the invention, the length (L') of the proximal zone (20') of the conductive layer is greater than the length (L") of the distal zone (20") of the conductive layer. More particularly, the length (L') of the proximal zone (20') of the conductive layer is approximately twice the length (L") of the distal zone (20") of the conductive layer.

According to the invention, the increase in the gap (e1) and/or the decrease in the gap (e2) between each distal electrode part (21", 22") can have a frustoconical shape. In this case, it is possible for at least one truncated cone to adjoin two parallel portions of distal electrode parts (21", 22"), as is illustrated in FIG. 6b.

According to the invention, the increase in the gap (e1) and/or the decrease in the gap (e2) between each distal electrode part (21", 22") has a curved shape. In this case, it is possible for the shape of the two distal electrode parts (21", 22") to be inscribed on an ellipse, the major axis of which is preferably the longitudinal axis (A) of the conductive layer. The ellipse can be a circle in one particular case.

The ellipse is illustrated in FIG. 6a. The leak detection capacity seems to be greater in the case of an ellipse rather than a truncated cone shape, especially if the needle is inserted at a large angle of incidence relative to the skin. The reason is that cutting the distal zone in a substantially elliptical shape and/or the elliptical shape of the electrodes permits, compared to an embodiment with frustoconical electrodes and/or cutting of the distal zone in a substantially rectangular shape, a folding of the probe in the longitudinal axis (A) of the probe and permits better detection of the fluid. This is because the probe more easily adapts to the shape of the fistula in the patient's arm.

According to the invention, the probe can have the following two zones: a proximal probe part (1') and a distal probe part (1"), where the proximal probe part (1') is superimposed with the proximal zone (20') of the conductive layer, and the distal probe part (1") is superimposed with the distal zone (20") of the conductive layer. In this case, the greater width (1") of the distal part (1") of the probe can be substantially twice the constant width (1') of the proximal part (1') of the probe.

Figure 7A:
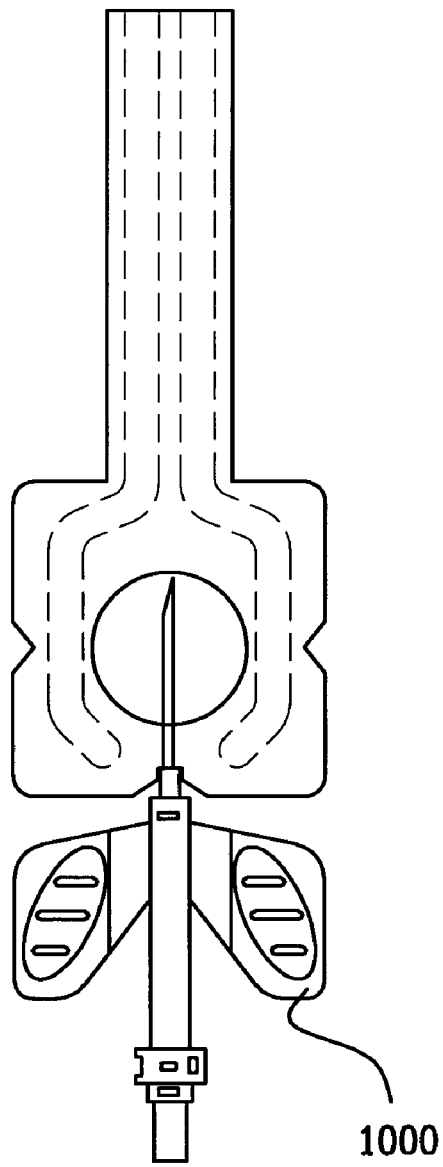
FIGS. 7a and 7b show two embodiments of the probe in the position of use on the needle inserted into the patient.
Figure 7B:
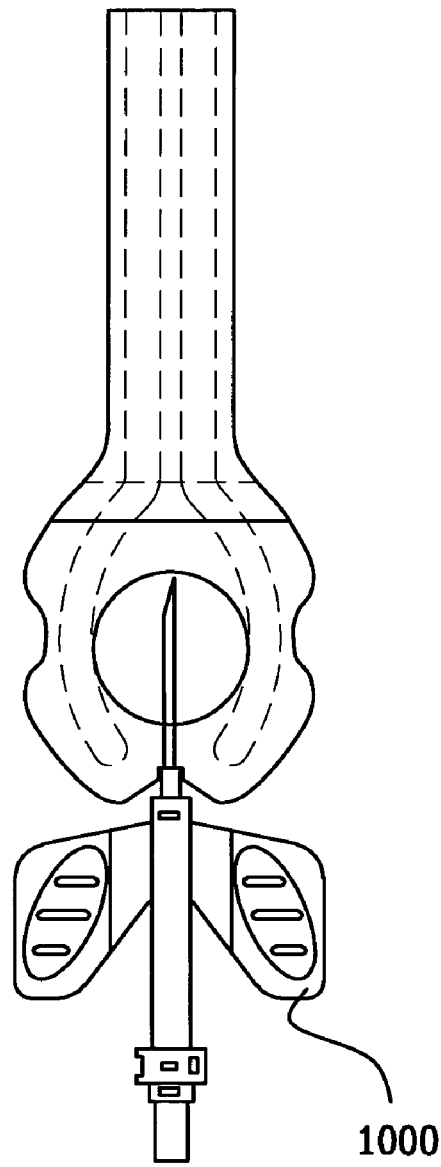

Moreover, as regards the general shape of the entire probe:
the edges of the distal part 1" of the probe can have a substantially elliptical shape, as is shown in FIG. 7b.
alternatively, the edges of the distal part 1" of the probe have a substantially rectangular shape, as is shown in FIG. 7a, or even square.

The probe according to the invention can comprise a hydrophilic layer 30 on at least part of the conductive layer 20. The presence of the hydrophilic layer ensures adsorption and retention of the conductive fluid at the distal zone of the conductive layer. It also allows the fluid to be detected to undergo internal lateral diffusion as far as the two detection electrodes.

According to the invention, one or more of the following features can be adopted:
the hydrophilic layer 30 can cover the distal zone 20" of the conductive layer,
the hydrophilic layer 30 can cover only the distal zone 20" of the conductive layer,
the hydrophilic layer 30 entirely covers the distal zone 20" of the conductive layer.

The probe can thus comprise a covering layer 40 intended to be in contact with the skin and on top of at least a part of the conductive layer 20.

The use of this layer is intended to isolate the patient's skin from the conductive layer, and to cover and protect at least the conductive layer left uncovered by the hydrophilic layer. According to one of the features of the invention concerning the covering layer:
the covering layer 40 is placed on top of substantially the entire proximal zone 20' of the conductive layer,
according to the preceding feature: the covering layer 40 can extend over a part of the distal zone 20' of the conductive layer,
according to the preceding feature: the covering layer 40 can be placed in contact on substantially the entire proximal zone 20' of the conductive layer and can be superimposed on and in contact with a part of the hydrophilic layer 30.

The expression "substantially the entire" is used because, in one particular embodiment, the covering layer 40 does not cover the proximal end (211', 221') of the proximal part (21', 22') of each electrode, in order to permit access to each uncovered end, called the contact end (211', 221'). Thus, the contact surface area of this contact end is sufficient to permit electrical contact with the conductive jaws of an electrical connector clip intended to connect each probe to the electrical measurement circuit. Embodiments other than this example will be evident to a person skilled in the art in order to permit electrical contact between the clip and the contact ends: for example, the covering layer could cover these contact ends but not be glued to these contact ends.

According to the invention, the edge 41 of the covering layer 40 which covers the distal zone 21" of the conductive layer can be perpendicular to the longitudinal axis (A) of the electrodes. This edge 41 designates the proximal edge of the covering layer, which is not necessarily aligned on the contour of the electrode.

A second covering layer could conceivably be used to cover the support layer.

The described series of layers defines layers that are placed on one another and that are in contact with one another according to the described order of positioning.

According to the invention, the length (L') of the proximal zone (20') of the conductive layer is greater than the length (L") of the distal zone (20") of the conductive layer. More particularly, the length L' of the proximal zone (20') of the conductive layer is approximately twice the length (L") of the distal zone (20") of the conductive layer.

According to the invention, the materials of each layer used are flexible materials.

The hydrophilic layer can be composed of a material of the compress type, for example of viscose, or of viscose and polyethylene, in the form of a woven, nonwoven or foam structure. It must have a thickness sufficient to absorb fluid and to improve and accelerate the absorption of fluid present at its surface, either laterally or in the direction of its thickness. The presence of small holes through the layer makes it possible in particular to improve adsorption. The thickness and compression capacity of this layer permits better distribution, across the skin surface, of the pressure induced by the adhesive tapes of the sticking plaster type, which will be attached to the probe in order to fix it to the arm.

The conductive layer must be as fine as possible in order to reduce the rigidity of the probe while at the same time maintaining continuous electrical conduction. It can be a laminated layer of conductive metal alone or of conductive metal on a polymer substrate; it can be made of aluminium placed on polyester. The proximal part of the conductive layer is long, not very wide and not very thick, and should have low rigidity in order to allow fairly easy distortion thereof so as to reduce the mechanical stresses applied to this zone and due in particular to the attachment of a device such as an electrical clip. However, the contact ends, which are wider than the rest of the proximal zone, mean that the connection surface does not distort and can be easily inserted into a clip.

The support layer can be composed of a nonwoven material. It must be as fine as possible in order to reduce rigidity and to permit contact of the probe along the entire surface of the patient's arm. This layer and the adhesive layer on top can be electrically insulating or have a high electrical resistance value when the probe is dry. It would also be conceivable to have a support layer that is also an absorbent layer. This layer will preferably have low extensibility in order to preserve the mechanical dimensions of the probe during the method of manufacture by assembly of the layers, since this layer has a support and transport function during manufacture.

The covering layer can be composed of a nonwoven material. This layer is a layer that covers and in particular preserves the electrodes. Moreover, it prevents the electrodes from coming into contact with the patient's skin, especially when a current passes through the electrodes. This layer and the adhesive applied to it, in order to fix it to the face of the conductive layer, act as an electrical insulator or electrical resistor of very high value in order to permit great resistance to the dry sensor (probe). In so far as this layer covers the proximal part of the electrodes, this layer can be hydrophobic so as to prevent false alarms due to the presence of fluid between only the proximal parts of the electrodes, for example because of residues of disinfectant or because of the patient's sweat.

The support layer and the covering layer can be composed of the same material, even of the same sheet of material.

According to the invention, the two electrodes (21, 22) can be in the form of conducting strips of substantially constant width. Each of the two strips can be continuous, made in one piece.

Thus, the probe can have at least one notch 100 made on the edge of the distal part (1") of the probe. In this case, at least said notch 100 is placed on an axis among the following: the longitudinal axis (A) of the probe, and an axis perpendicular to the longitudinal axis of the probe and passing substantially through the middle of the proximal zone of the probe. As is illustrated in FIGS. 7a and 7b, this notch makes it possible to maintain the needle or tube inserted in the patient. The notch made on the edge of the probe can in fact be in the form of a half disc or of a triangle or rectangle, simply a slit, or a slit followed by an orifice, the orifice having another geometrical shape for receiving and fixing the section of the needle (1000) inserted in the patient, for example a disc.

The probe can comprise two or three notches, or even more, depending on the position of use of the probe relative to the needle and relative to the angle of insertion of the needle.

Figure 8:
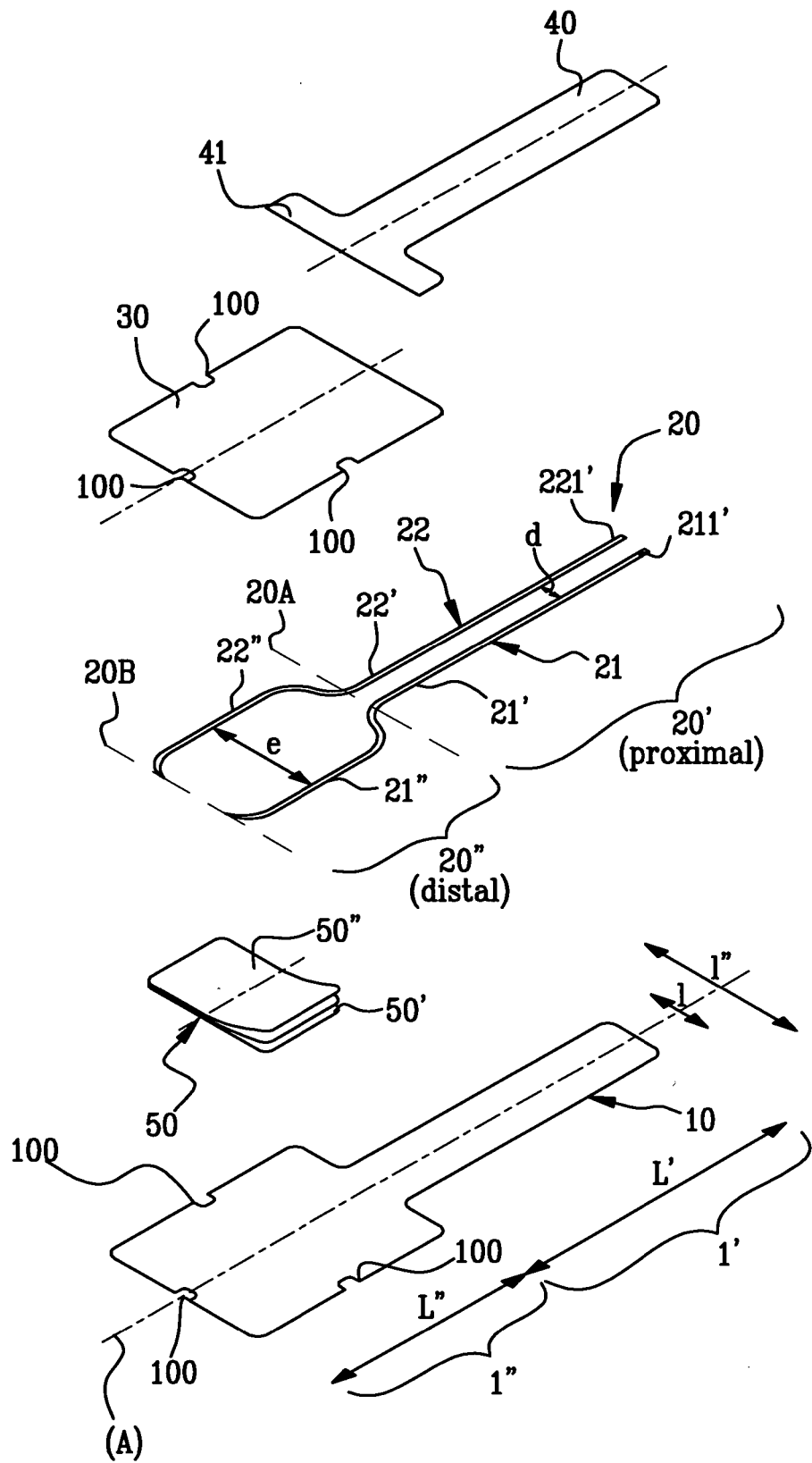
FIG. 8 shows an exploded view of one of the embodiments of the probe according to the invention that operates by detecting the electrical resistance and capacitance between the electrodes.
Figure 9:
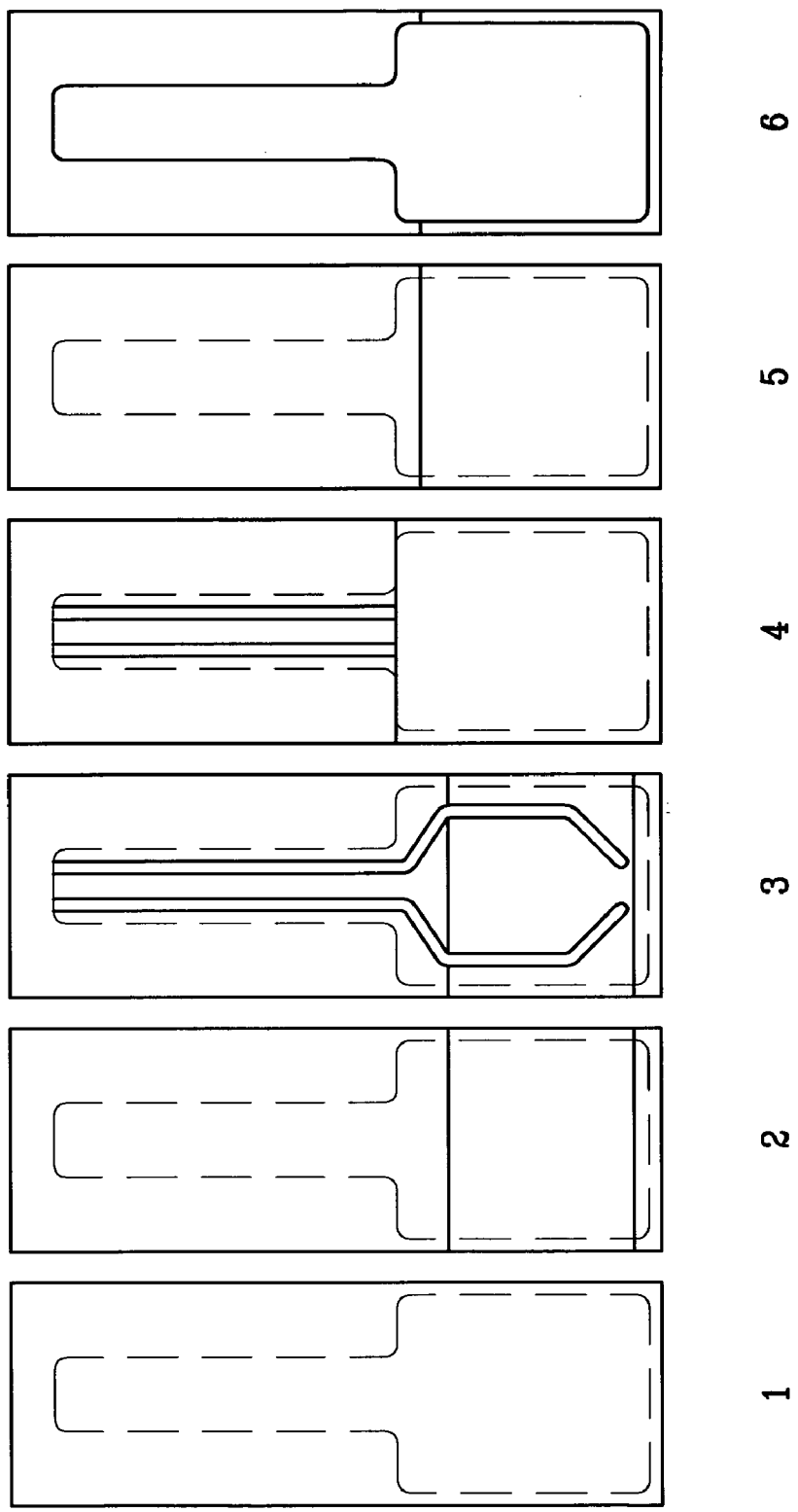
FIG. 9 shows the different layers of the probe according to FIG. 8 manufactured step by step.

Another embodiment of the improved probe is shown in FIGS. 8 and 9 and is the following: the probe comprises a supplementary layer called the capacitor layer 50 positioned between the support layer and the conductive layer, comprising:

a conductive first capacitor layer 50' placed on the support layer 10, an insulating second capacitor layer 50" placed on the conductive first capacitor layer 50'.

According to this capacitor proposal:

the conductive first capacitor layer 50' and the insulating second capacitor layer 50" can be made up of a single part 50 which thus has a conducting face ("outer" face) and an insulating face ("inner" face);

the capacitor layer 50 can at least partially cover the distal zone of the conductive layer 20. In this case, the capacitor layer 50 can cover the part of the distal zone of the conductive layer 20 in which the gap between the distal parts of the electrodes is the greatest. The layer can alternatively cover substantially the entire distal zone. The layer can cover only the distal zone of the electrodes (without covering the proximal zone).

Figure 10:
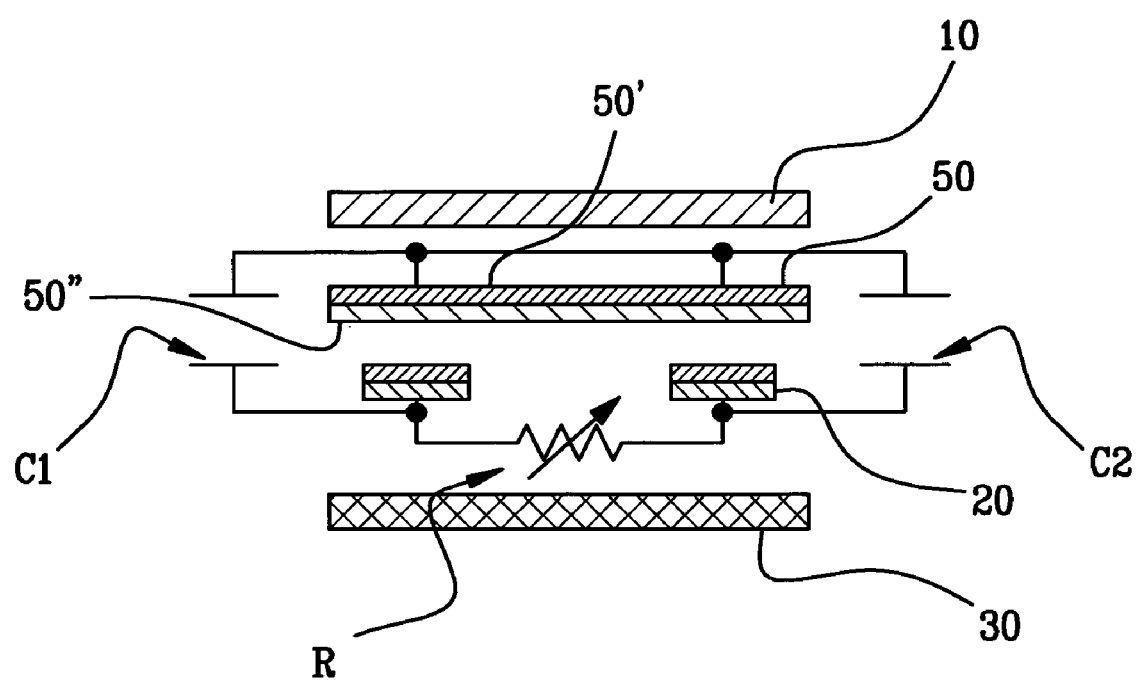
FIG. 10 shows the electrical diagram of the probe from FIG. 8.

The capacitor layer permits formation of a resistor/capacitor circuit in parallel in the area of the probe, as is illustrated in FIG. 10. The illustration shows that the capacitor layer 50 inserted between the conductive layer 20 and the support layer 10 will form two capacitors (C1, C2): the first (C1) between, on the one hand, the first electrode and the capacitor layer, and the second (C2), on the other hand, the second electrode of the capacitor layer. The characteristics of C1 and C2 can of course be calculated by the insulating distance that separates them from the conductive layer and by their surface area. This supplementary layer produces, between the two contact electrodes, an electrical circuit of variable resistance R (depending on the presence of fluid) in parallel with a total capacitor. This makes it possible to form an individual probe that can self-test when connected to the measurement circuit, hence at any time during use of the probe. The impedance of the probe can be measured, and the addition of a capacitor delivers electrical information completely independent of that used for detection of fluid—the resistance. Thus, the stability of the capacitance value is less critical, and many methods of impedance measurement known to a person skilled in the art can be used to measure the impedance at any time during the use of the probe. There are a total of four cases where the capacitance measured makes it possible to deduce the state of the probe.

In a first case, the probe is normal, the resulting capacitor C has a value C1 in series with C2, that is to say $C=C1*C2/(C1+C2)$. Hence, $C=C1/2=$Cnormal in the particular case of configuration where $C1=C2$. In a second case, the probe has a rupture (electrical non-continuity) at the connection zone (proximal zone) on at least one of the electrodes, in this case the electrical continuity is not provided, the capacitors are still in series but connected to only one of the external contacts, hence $C=0<=$Cnormal.

In a third case, the probe has a rupture (electrical non-continuity) at the detection zone (distal zone) on at least one of the electrodes, in this case the value of at least one of the two capacitors is only X% of its normal value, in this case the resulting capacitor C still has a value $C=C1*C2/(C1+C2)$ but, if this decrease applies to C2, for example $C2=C1*X$, then the value of the final capacitor is $C=C1*C1*X/(C1+(X*C1))$, hence $C=C1*(X/(1+X))<=$Cnormal. This phenomenon is amplified especially for $0.5<X<1$, because of the connection in series.

In a fourth case, the probe has a short circuit (electrical continuity) at the detection zone (distal zone) between one and only one of these electrodes and the conductive layer of the capacitor, in this case the value of at least one of the two capacitors is infinite in the electrical sense, in this case the resulting capacitor C still has the value $C=C1*C2/(C1+C2)$ but if C2 is infinite then: $C=C1>=Cnormal$. For this case, the presence of a single short circuit does not prevent the probe from functioning and detecting fluids.

In the case of a short circuit for each of the two electrodes with the capacitor layer, the resistance of the probe becomes zero (detectable) and there is no longer any measurable capacity in parallel.

The capacitor value in the normal state will have to be fixed as high as possible, and the thickness between the two electrically active layers must be as low as possible.

Alternatively, the capacitor layer 50 can be replaced by two layer elements (identical to the single capacitor layer 50 with respect to the definition of layers) placed exclusively on top of the existing electrodes 30.

This capacitor layer alternative could be envisaged on a simple configuration comprising a support layer 10, a conductive layer 20 with two electrodes, without the conductive layer having a particular configuration as described above. The conductive layer could comprise two parallel electrodes as described in the prior art document U.S. Pat. No. 5,557,263 or two electrodes with an increased gap, as described in prior art document U.S. Pat. No. 6,175,310, these being incorporated herein by reference. All that is described concerning this capacitor applies to these two probes.

Moreover, the insulating layer placed between the conductive layer of electrodes and the conductive layer of the capacitor can instead be replaced by an adhesive layer sufficiently thick to represent an insulating layer.

According to one feature of the invention, the probe can be sterilized. It can be inserted into an individual package, and the sterilization takes place once the probe has been placed in the package. The sterilization can be a sterilization of the gamma sterilization type, or sterilization with ethylene oxide.

A non-limiting example of the dimensions of the probe may be given. The distal part of the probe can be a square whose side measures between approximately 30 and 40 mm. Alternatively, the distal part is an ellipse whose major axis measures approximately 40 mm and whose minor axis measures 30 mm. The maximum spacing e between the two distal parts of the electrodes can be equal to approximately 20 mm, the distance between two proximal parts of the electrodes can be equal to 3 mm. The length of the proximal zone can be equal to approximately 60 mm, the width of the proximal zone can be equal to approximately 14 mm. The width of the proximal parts (21') of the electrodes can be equal to 3.5 mm, the length of the contact ends of the proximal parts of the electrodes can be equal to approximately 10 mm. When the electrodes are in the form of strips the width of the strip can be equal to approximately 3.5 mm.

As regards the assembly of the probe according to the invention:
- one face of the support layer 10 (the face which will be in contact with the conductive layer, the "inner" face, that is to say the face directed towards the skin when the probe is in use) can be covered with adhesive so as to fix it to one face of the conductive layer 20 and to that part of one face of the hydrophilic layer (outer face) in direct contact with said face of the support layer 20,
- one face of the covering layer 40 (the "outer" face) is covered with adhesive so as to fix it to at least a part of one face ("inner" face) of the conductive layer's proximal zone 20' and optionally to fix it to a part of one face ("inner" face) of the hydrophilic layer 30.

This allows the different layers of the probe to be fixed without using too much adhesive, or too many layers of adhesive, at locations where the adhesive could prevent electrical conduction or could cause bulges. It is also an economic advantage. The adhesive used can be, for example, a hot-melt adhesive material and/or a pressure-sensitive adhesive.

The invention also relates to a method for the manufacture of a disposable medical probe for detecting a leak of physiological fluid through an opening made in the human body, by operating in conjunction with an electrical detection circuit, comprising the following steps:
a) obtaining a support layer 10,
b) placing a conductive layer 20 on top of the support layer 10, the conductive layer comprising two conducting electrodes (21, 22) both placed exclusively on each side of a longitudinal axis (A), the conductive layer 20 defining two zones:
- a proximal zone 20', the end of which is intended to be connected to said circuit, composed of a proximal part (21', 22') of each electrode, the two proximal electrode parts being placed parallel to each other and spaced apart by a substantially constant distance d,
- a distal zone 20" intended for possible contact with the fluid, composed of a distal part (21", 22") of each electrode (21, 22), the two distal electrode parts being symmetrical with respect to said longitudinal axis and spaced apart from each other by a gap e greater than said distance (d), where the distal zone 20" of the electrodes defines, running from the border 20A between the proximal zone and the distal zone to the end of the distal zone 20B:
- an increase in the gap e1 between the distal parts of the electrodes,
- followed by a decrease in the gap e2 between the distal parts of the electrodes.

The method can comprise an additional step c) which consists in cutting substantially all the edges of the probe by means of a single step of cutting the layers superimposed on one another. This single step guarantees that no accumulation of adhesive is present on the exposed outer surfaces of the probe, especially on the contact ends of the proximal zone of the electrodes.

Figure 5:
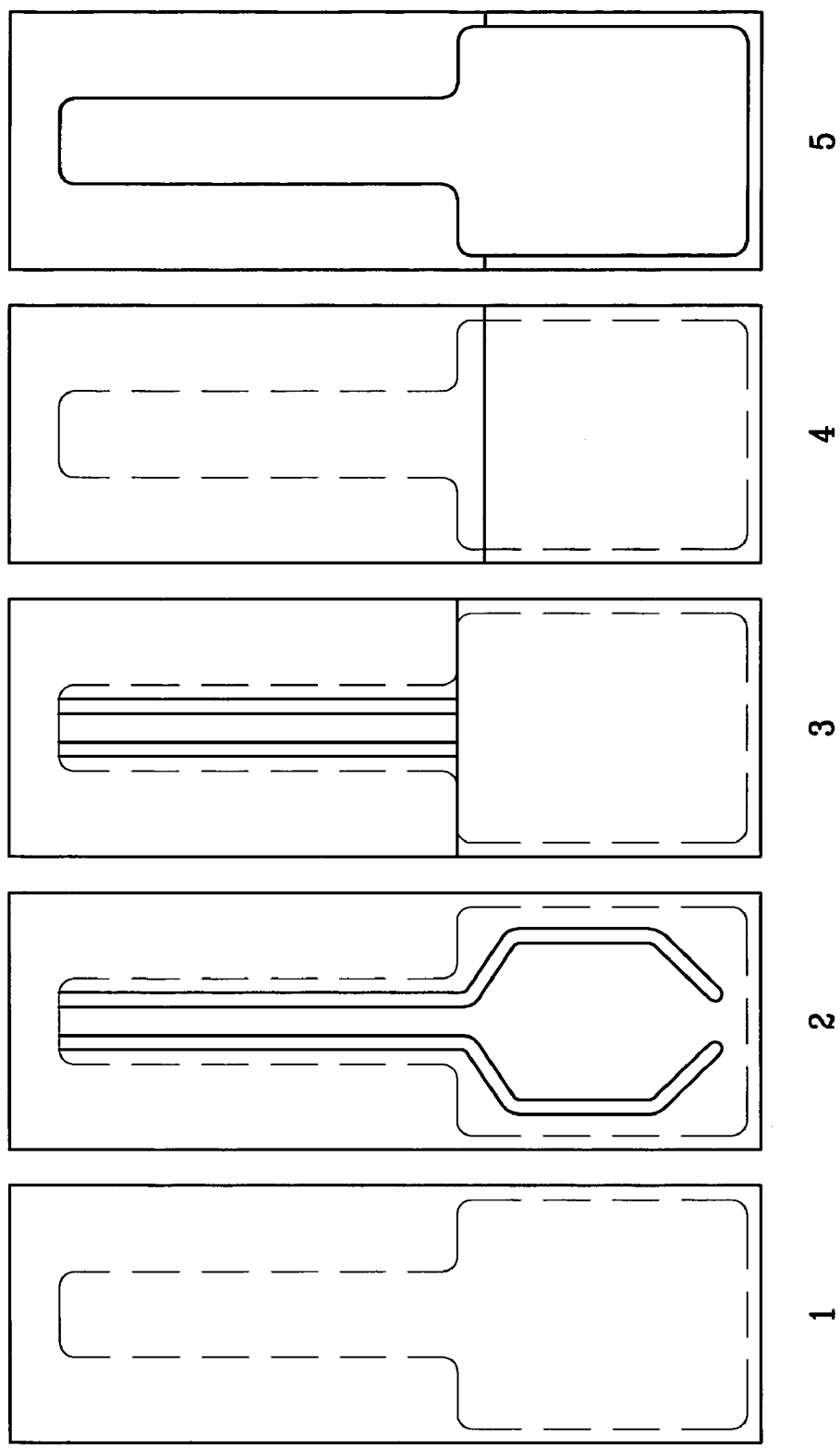
FIG. 5 shows the different layers of the probe according to FIG. 4 manufactured step by step.

Steps a, b, c are shown in FIGS. 5 and 9. FIG. 9 illustrates the probe embodiment containing a supplementary layer called a capacitor layer, which would be inserted in a step b') after deposition of the conductive layer (step b). The method can comprise the step of placing a hydrophilic layer 30 on the conductive layer 20 and/or a step of placing a covering layer 40 on the conductive layer 20, and/or the hydrophilic layer where appropriate, and/or on the capacitor layer where appropriate. The method can also comprise at least one of the following steps: the step of applying adhesive to one face of the support layer (see FIG. 9); the step of applying adhesive to one face of the covering layer 40.

As regards the method of using the probe according to the invention, it proceeds as follows step by step:
- the user inserts the needle into the fistula in the patient (optional step if the aim is to detect the opening of a wound, for example),
- the user positions the probe once it has been removed from its individual package, and if a notch is present, the user will position the section of the needle in the notch,
- the user will glue one or several adhesive strips to the probe, preferably on the distal part of the probe, for example two sticking plasters in a cross shape, the user will then fix to the contact ends of the probe the connector clip for electrical connection, in order to establish the electrical detection circuit.

This disposable probe will be disposed of at the end of the session.

The probe according to the invention can also have the following features: a disposable medical probe 1 for detecting a leak of physiological fluid through an opening made in the human body, by operating in conjunction with an electrical detection circuit, comprising the following layers: support layer (10), a conductive layer (20) on top of the support layer (10), the conductive layer comprising two conducting electrodes (21, 22) both placed exclusively on each side of a longitudinal axis, a hydrophilic layer (30), intended to receive a possible physiological fluid, on top of at least a part of the conductive layer (20), the conductive layer (20) defining two zones: a proximal zone (20'), the end of which is intended to be connected to said electrical circuit, composed of a proximal part (21', 22') of each electrode, the two proximal electrode parts being placed parallel to each other and spaced apart by a distance d, a distal zone (20") intended for contact with the possible fluid, composed of a distal part (21", 22") of each electrode (21, 22), the two distal electrode parts being symmetrical with respect to said longitudinal axis and being spaced apart from each other by a gap (e) greater than the distance d.

It will have all the possible supplementary features described above.

The corresponding method of manufacture will be a method for the manufacture of a disposable medical probe for detecting a leak of physiological fluid through an opening made in the human body, by operating in conjunction with an electrical detection circuit, comprising the following steps:

a) obtaining a support layer 10,
b) placing a conductive layer 20 on top of the support layer 10, the conductive layer comprising two conducting electrodes (21, 22) both placed exclusively on each side of a longitudinal axis (A), the conductive layer 20 defining two zones:
   a proximal zone (20'), the end of which is intended to be connected to said circuit, composed of a proximal part (21', 22') of each electrode, the two proximal electrode parts being placed parallel to each other and spaced apart by a constant distance (d),
   a distal zone (20") intended for contact with the possible fluid, composed of a distal part (21", 22") of each electrode (21, 22), the two distal electrode parts being symmetrical with respect to said longitudinal axis and spaced apart from each other by a gap (e) greater than said distance (d),
c) placing a hydrophilic layer (30), intended to receive a possible physiological fluid, on top of at least a part of the conductive layer (20).

This method will be able to comprise all the possible subsequent steps described below.

ADVANTAGES OF THE INVENTION

The advantages of the probe according to the invention are many and are listed here:
- improving the flexibility of the probe to be placed on the patient's skin,
- optimizing the connection between the probe and the rest of the electrical measurement circuit,
- increasing patient comfort,
- improving the degree of freedom for fixing the probe to the skin,
- detecting poor insertion or inadequate insertion of an electrical connector clip,
- avoiding unnecessary adhesive on the probe,
- using the fewest possible layers of material and of adhesive for the probe,
- providing a probe that is able to allow the electrical circuit to carry out a self-test on the state of the probe and the connection of the probe,
- making available a manufacturing method that is simple, rapid and effective, especially in terms of cutting,
- making available a disposable probe that is well adapted for sterile individual packaging.

The invention claimed is:

1. A disposable medical probe for detecting a leak of physiological fluid through an opening made in the human body, by operating in conjunction with an electrical detection circuit, comprising the following layers:
   a support layer,
   a conductive layer on top of the support layer (10), the conductive layer comprising first and second conducting electrodes, said first conducting electrode being placed on one side of a longitudinal axis and said second conducting electrode being placed on the opposite side of the longitudinal axis, the conductive layer defining two zones:
   a proximal zone, the end of which is configured to be connected to said circuit, said proximal zone comprising a proximal part of each of the first and second electrodes, the proximal parts of the first and second electrodes being placed parallel to each other and spaced apart by a distance
   a distal zone configured to contact a fluid, said distal zone comprising a distal part of each of the first and second electrodes, the distal parts of the first and second electrodes being spaced apart from each other by a gap, said gap being greater than said distance,
   where the distal zone of the first and second electrodes defines, running from a border, positioned between the proximal zone and the distal zone, to the end of the distal zone,
   an increase in the gap between the distal parts of the first and second electrodes,
   followed by a decrease in the gap between the distal parts of the first and second electrodes.

2. A probe according to claim 1, wherein there is a constant gap between the distal parts of the first and second electrodes, positioned between said increase in the gap and said decrease in the gap.

3. A probe according to claim 1, wherein the longitudinal axis is an axis of symmetry of substantially the entirety of the first and second electrodes.

4. A probe according to claim 3, wherein the axis of symmetry of the first and second electrodes represents the axis of symmetry of substantially the entire probe.

5. A probe according to claim 1, wherein the length of the proximal zone of the conductive layer is greater than the length of the distal zone of the conductive layer.

6. A probe according to claim 5, wherein the length of the proximal zone of the conductive layer is approximately twice the length of the distal zone of the conductive layer.

7. A probe according to claim 1, wherein at least one of the increase in the gap and the decrease in the gap between each of the distal parts of the first and second electrodes has a frustoconical shape.

8. A probe according to claim 7, wherein at least one truncated cone is adjacent to first and second parallel portions of the distal parts of the first and second electrodes.

9. A probe according to claim 1, wherein at least one of the increase in the gap and the decrease in the gap between each of the distal parts of the first and second electrodes has a curved shape.

10. A probe according to claim 9, wherein the shape of the distal parts of the first and second electrodes is inscribed on an ellipse, the major axis of which is the longitudinal axis of the conductive layer.

11. A probe according to claim 1, further comprising
the following two zones: a proximal probe part and a distal probe part, and
wherein the proximal probe part is superimposed with the proximal zone of the conductive layer, and the distal probe part is superimposed with the distal zone of the conductive layer.

12. A probe according to claim 11, wherein the greater width of the distal part of the probe is substantially twice the constant width of the proximal part of the probe.

13. A probe according to claim 11, wherein the edges of the distal part of the probe have a substantially elliptical shape.

14. A probe according to claim 11 or 12, wherein the edges of the distal part of the probe have a substantially rectangular shape.

15. A probe according to claim 1, comprising a hydrophilic layer on at least a part of the conductive layer.

16. A probe according to claim 1, comprising a covering layer on at least a part of the conductive layer.

17. A probe according to claim 1, wherein the length of the proximal zone of the conductive layer is greater than the length of the distal zone of the conductive layer.

18. A probe according to claim 1, wherein the materials of which each layer are made are flexible materials.

19. A probe according to claim 1, wherein the first and second electrodes are in the form of conducting strips of substantially constant width.

20. A probe according to claims 11, wherein at least one notch is made on the edge of the distal part of the probe.

21. A probe according to claim 20, wherein at least said notch is placed on at least one axis among the following: the axis of symmetry of the probe, an axis perpendicular to the axis of symmetry of the probe and passing substantially through the middle of the proximal zone of the probe.

22. A probe according to claim 1, comprising a capacitor layer positioned between the support layer and the conductive layer, said capacitor layer comprising:
a conductive first capacitor layer placed on the support layer,
an insulating second capacitor layer placed on the conductive first capacitor layer.

23. A probe according to claim 22, wherein the conductive first capacitor layer and the insulating second capacitor layer make up a single part having a conducting face and an insulating face.

24. A probe according to claim 22, wherein the capacitor layer at least partially covers the distal zone of the conductive layer.

25. A probe according to claim 24, wherein the capacitor layer covers a portion of the distal zone of the conductive layer in which the gap between the distal parts of the first and second electrodes is the greatest.

26. A probe according to claim 1, wherein the probe is sterilized.

27. A method for the manufacture of a disposable medical probe for detecting a leak of physiological fluid through an opening made in a human body, by operating in conjunction with an electrical detection circuit, comprising the following steps:
obtaining a support layer,
placing a conductive layer on top of the support layer, the conductive layer comprising first and second conducting electrodes, said first electrode positioned on one side of a longitudinal axis and said second electrode positioned on the opposite side of the longitudinal axis, the conductive layer defining the following two zones:
a proximal zone, the end of which is configured to be connected to said circuit, said proximal zone composed of a proximal part of each of the first and second electrodes, the proximal parts of the first and second electrodes being placed parallel to each other and being spaced apart by a substantially constant distance; and
a distal zone configured to contact a fluid, said distal zone composed of a distal part of each of the first and second electrodes, the distal parts of the first and second electrodes being spaced apart from each other by a gap being greater than said distance;
where the distal zone of the first and second electrodes defines, running from a border, positioned between the proximal zone and the distal zone, to the end of the distal zone:
an increase in the gap between the distal parts of the first and second electrodes,
followed by a decrease in the gap between the distal parts of the first and second electrodes.

28. A method according to claim 27, further comprising cutting substantially all the edges of the probe by means of a single step of cutting the layers superimposed on one another.

* * * * *

UNITED STATES PATENT AND TRADEMARK OFFICE
CERTIFICATE OF CORRECTION

PATENT NO. : 8,217,218 B2
APPLICATION NO. : 12/922400
DATED : July 10, 2012
INVENTOR(S) : Thierry Court, Jean Michel Goby and Jean Pierre Anselmet It is certified that error appears in the above-identified patent and that said Letters Patent is hereby corrected as shown below:

Claim 1, Column 12, Line 31, insert --,-- after "distance".

Claim 20, Column 13, Line 36, "claims" should be "claim".

Signed and Sealed this
Twenty-fifth Day of September, 2012

David J. Kappos
*Director of the United States Patent and Trademark Office*